(12) United States Patent
Kim

(10) Patent No.: US 10,590,378 B2
(45) Date of Patent: Mar. 17, 2020

(54) CELL SEPARATION CHIP AND METHOD FOR SEPARATING CELLS USING SAME

(71) Applicant: FERRAMED INC., Daejeon (KR)

(72) Inventor: Seyl Kim, Daejeon (KR)

(73) Assignee: FERRAMED INC., Daejeon (KR)

( * ) Notice: Subject to any disclaimer, the term of this patent is extended or adjusted under 35 U.S.C. 154(b) by 175 days.

(21) Appl. No.: 15/564,008

(22) PCT Filed: Apr. 11, 2016

(86) PCT No.: PCT/KR2016/003781
§ 371 (c)(1),
(2) Date: Oct. 3, 2017

(87) PCT Pub. No.: WO2016/163844
PCT Pub. Date: Oct. 13, 2016

(65) Prior Publication Data
US 2018/0135005 A1    May 17, 2018

(30) Foreign Application Priority Data
Apr. 9, 2015 (KR) .................... 10-2015-0050023

(51) Int. Cl.
*C12M 1/00* (2006.01)
*C12M 1/12* (2006.01)
(Continued)

(52) U.S. Cl.
CPC .............. *C12M 47/04* (2013.01); *C12M 1/12* (2013.01); *C12M 47/02* (2013.01); *C12Q 1/24* (2013.01);
(Continued)

(58) Field of Classification Search
CPC ........ C12M 1/12; C12M 47/02; C12M 47/04; C12Q 1/24; G01N 15/1031; G01N 1/40; G01N 1/4005
See application file for complete search history.

(56) References Cited

U.S. PATENT DOCUMENTS 5,804,128 A * 9/1998 Ogata ................... B01D 29/111
                                                         210/494.1
6,641,708 B1   11/2003 Becker et al.
(Continued)

FOREIGN PATENT DOCUMENTS

JP        2011-095164 A    5/2011
KR    10-2007-0110581 A   11/2007
(Continued)

OTHER PUBLICATIONS

International Search Report for PCT/KR2016/003781.
(Continued)

*Primary Examiner* — Jennifer Wecker
(74) *Attorney, Agent, or Firm* — The PL Law Group, PLLC

(57) ABSTRACT

A cell separation chip for separating cells from a solution containing the cells includes an upper plate, a membrane positioned on a predetermined region of the upper plate, and an absorption device positioned at a lower end of the upper plate so as to absorb a solution which has penetrated the membrane from the solution containing the cells. There is an effect of effectively collecting/separating only cells in a solution by absorbing the solution containing the cells without the need of applying and maintaining additional external voltage.

8 Claims, 3 Drawing Sheets

(51) Int. Cl.
  *C12Q 1/24* (2006.01)
  *G01N 15/10* (2006.01)
  *G01N 1/40* (2006.01)

(52) U.S. Cl.
  CPC ............ *G01N 1/40* (2013.01); *G01N 1/4005* (2013.01); *G01N 15/1031* (2013.01)

(56) References Cited

U.S. PATENT DOCUMENTS

2007/0178521 A1* 8/2007 Sakaino ............ B01L 3/502753
 435/7.1
2009/0120865 A1* 5/2009 Chung .............. B01L 3/502753
 210/232
2010/0248351 A1* 9/2010 Seyama ............ B01L 3/502715
 435/288.7

FOREIGN PATENT DOCUMENTS

| KR | 10-2009-0049414 A | 5/2009 |
| KR | 10-2012-0042532 A | 5/2012 |
| WO | WO 2004/055170 A1 | 7/2004 |

OTHER PUBLICATIONS

Xiaoyuan Hu et al., "Marker-specific sorting of rare cells using dielectrophoresis", PNAS, vol. 102, No. 44, Nov. 2005, pp. 15757-15761.

\* cited by examiner

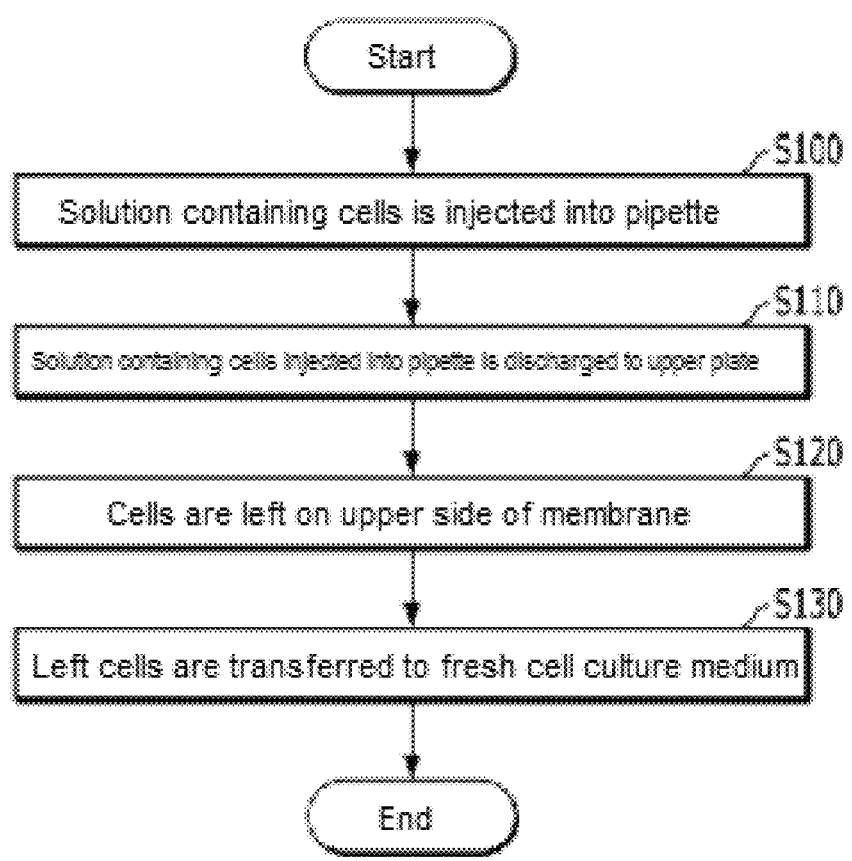

CELL SEPARATION CHIP AND METHOD FOR SEPARATING CELLS USING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/003781, filed Apr. 11, 2016, which claims priority to the benefit of Korean Patent Application No. 10-2015-0050023 filed in the Korean Intellectual Property Office on Apr. 9, 2015, the entire contents of which are incorporated herein by reference.

TECHNICAL FIELD

The present disclosure relates to a cell separation chip and a method for separating cells using the same. More particularly, it relates to a cell separation chip capable of effectively collecting/separating only cells in a solution by absorbing the solution containing the cells without the need of applying and maintaining additional external voltage and a method for separating cells using the same.

The cell separation chip and the method for separating cells using the same according to the present disclosure can be applied to a diagnostic lab-on-a-chip with integrated cell separation and analysis functions.

BACKGROUND ART

In general, a biochemical sample contains more than two different materials. Therefore, a separation technique of separating specific components from a mixture for analysis or purification of the components is very important in a sample pretreatment process.

In particular, also in a lab-on-a-chip, wherein microchannels, mixers, pumps, valves, etc. are integrated on a single chip for high-throughput analysis of a small quantity of sample, the sample preparation processes such as purification and separation are key processes that should precede the analysis process.

And, cell-based diagnostics which is important in biological or medical assays embraces blood analysis, cell research, microbiological analysis and tissue transplantation. With the recent development of cell research, cell analysis and protein/DNA analysis techniques, studies on unification and integration of such a clinical diagnostic procedure in the form of a microfluidic device are being conducted.

The microfluidic device for clinical diagnosis refers to a single device in which a series of processes of separating and observing cells to be analyzed, lysing the separated cells and analyzing proteins and DNAs extracted from the cells are integrated. The separation of cells to be analyzed from a sample in which two or more different cells are mixed is an essential procedure to acquire accurate clinical information. For this, a method for separating cells based on microfluidics using the intrinsic difference in physical and chemical properties of cells has been proposed.

Dielectrophoretic separation is based on the difference in dielectrophoretic force occurring when cells are exposed to a non-uniform electric field. U.S. Pat. No. 6,641,708 proposes a method for separating leukocytes using a thin-film chamber forming a velocity profile. Also, a method capable of separating rare target cells with high efficiency by specifically labeling cells with marker particles capable of amplifying the dielectrophoretic force has been reported (*PNAS* 102; 15757, 2005).

However, although the dielectrophoretic separation allows separation of nonpolar particles and cells without a pretreatment process, a cell-friendly solution cannot be used for the separation because electrolysis may occur in an electrolytic solution such as a cell medium. In addition, for a biological sample containing cells, the separated cells cannot be used for cell therapy because the activity of the cells is affected by the applied voltage.

Meanwhile, in passive separation, cells are separated by the energy required for feeding the sample, unlike the dielectrophoretic separation utilizing external electric field, based on the difference in the density and size of the cells. A cell separation chip used in this passive separation method should be able to separate the cells effectively while having a simple structure to allow easy manufacturing.

Accordingly, there is a need of a cell separation chip capable of effectively collecting/separating only cells in a solution by absorbing the solution containing the cells without the need of applying and maintaining additional external voltage and a method for separating cells using the same.

SUMMARY

The present disclosure has been made to solve the above-described problems and is directed to providing a cell separation chip capable of separation and diagnosis in short time using a solution containing cells.

The present disclosure is also directed to improving sample pretreatment to provide convenience in cell research, prevent mechanical loss of a research target and help development of biocontents for diagnosis of various diseases.

The present disclosure is also directed to providing a diagnostic lab-on-a-chip with integrated cell separation and analysis functions and a method for separating cells using the same.

The technical problems (purposes) to be solved by the present disclosure are not limited to those described above. Other problems (purposes) will be obviously understood by those of ordinary skill in the art to which the present disclosure belongs from the following description.

A cell separation chip and a method for separating cells using the same are disclosed. The cell separation chip for separating cells from a solution containing the cells according to the present disclosure includes: an upper plate; a membrane positioned on a predetermined region of the upper plate; and an absorption means positioned at a lower end of the upper plate so as to absorb a solution which has penetrated the membrane from the solution containing the cells. According to the present disclosure, there is an effect of effectively collecting/separating only cells in a solution by absorbing the solution containing the cells without the need of applying and maintaining additional external voltage.

The present disclosure provides the following effects.

The present disclosure allows separation and diagnosis in short time using a solution containing cells.

Also, the present disclosure provides the effect of provide convenience in cell research, preventing mechanical loss of a research target and helping development of biocontents for diagnosis of various diseases.

In addition, the present disclosure provides a diagnostic lab-on-a-chip with integrated cell separation and analysis functions and a method for separating cells using the same.

BRIEF DESCRIPTION OF DRAWINGS

FIG. 3 shows the flow chart of a method for separating cells according to the present disclosure.

DETAILED DESCRIPTION

Figure 1:
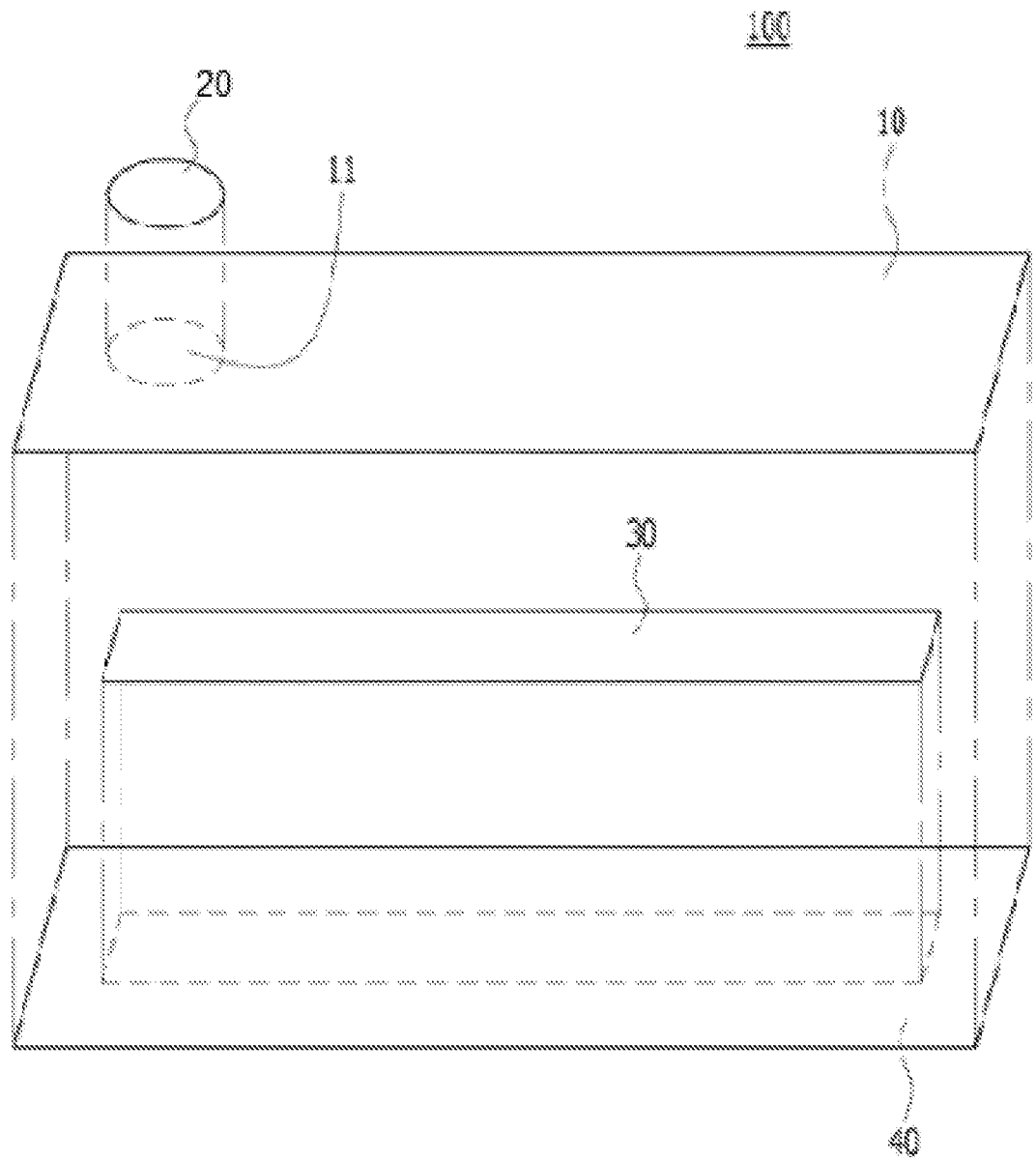
FIG. 1 shows the configuration of a cell separation chip according to the present disclosure.

In order to solve the problems described above, the present disclosure may provide a cell separation chip for separating cells from a solution containing the cells, including: an upper plate; a membrane positioned on a predetermined region of the upper plate; and an absorption means positioned at a lower end of the upper plate so as to absorb a solution which has penetrated the membrane from the solution containing the cells.

The cell separation chip may further include a lower plate positioned at the lower end of the upper plate by being connected to the absorption means.

The membrane may include: an upper end region forming an upper end of the membrane as a region where the solution containing cells is contacted first; and a lower end region forming a lower end of the membrane as a region where the solution is contacted with the absorption means.

The upper end region may have a hole with a diameter of 2 μm or smaller.

The lower end region may have a hole with a diameter of 10 μm or greater.

The upper plate may be formed of a film or a plastic.

The lower plate may be formed of a film or a plastic.

The absorption means may be formed of a filter paper or a glass fiber.

The predetermined region may have a circular shape and the membrane may also have a circular shape accordingly.

The membrane may be a plasma separation membrane.

The present disclosure may also provide a method for separating cells from a solution containing the cells using the cell separation chip according to the present disclosure, including: a step wherein a solution containing cells is injected into a pipette; a step wherein the solution containing cells injected into the pipette is discharged to the upper plate; and a step wherein cells from the solution containing cells are left on an upper side of the membrane.

The method may further include, after the step wherein the cells from the solution containing cells are left on an upper side of the membrane, a step wherein the left cells are transferred to a fresh cell culture medium.

MODE FOR INVENTION

The present disclosure can be embodied in various forms and various modifications may be made thereto. Specific exemplary embodiments are described in the following description and drawings.

However, the present disclosure is not limited by the specific exemplary embodiments but should be understood to comprehend all modifications, equivalents and substitutes included in the technical idea and scope of the present disclosure. In the attached drawings, like numerals are used to represent like elements.

It will be understood that when an element is referred to as being "connected" or "coupled" to another element, it can be directly connected or coupled to the element or other elements may be present therebetween. But, it will be understood that, if it is described that a certain element is "connected directly" or "coupled directly" to another element, no other element is present therebetween.

The terminology used in the present disclosure is for describing specific exemplary embodiments only and is not intended to limit the present disclosure. In the present disclosure, singular expressions are intended to include plural expressions unless the context clearly indicates otherwise. In the present disclosure, the expressions "include (contain)", "have", etc. specify the presence of stated features, numbers, steps, operations, members, elements or combinations thereof, but do not preclude the presence or addition of one or more other features, numbers, steps, operations, members, elements or combinations thereof.

Hereinafter, specific exemplary embodiments of the present disclosure are described in detail referring to the attached drawings. In the drawings, like numerals refer to like elements. In the following description, description about the same elements will be omitted to avoid redundancy.

Figure 2:
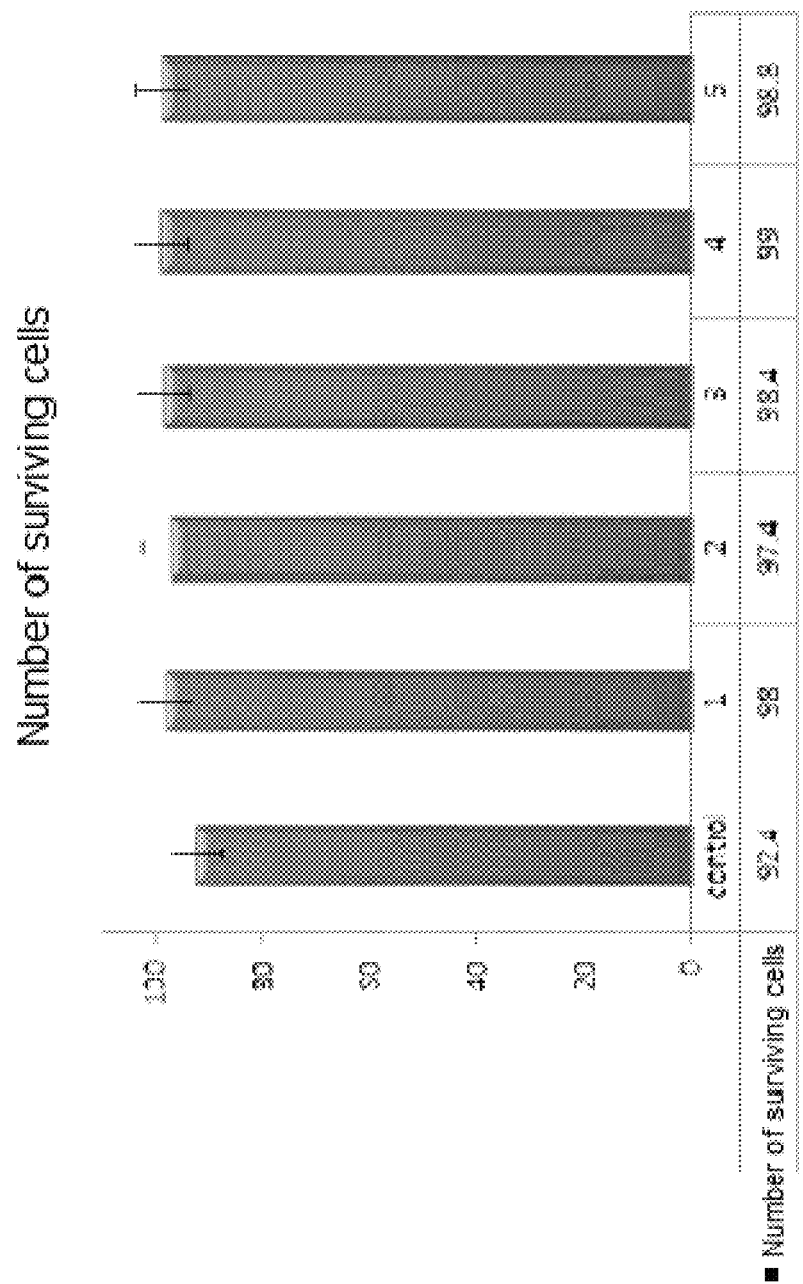
FIG. 2 shows the effect of a cell separation chip and a method for separating cells according to the present disclosure.

FIG. 1 shows the configuration of a cell separation chip according to the present disclosure. FIG. 2 shows the effect of a cell separation chip and a method for separating cells according to the present disclosure. FIG. 3 shows the flow chart of a method for separating cells according to the present disclosure.

Referring to FIG. 1, a cell separation chip 100 according to the present disclosure, which performs the function of effectively separating cells from a solution containing the cells, is composed largely of an upper plate 10, a membrane 20 and an absorption means 30 and a lower plate 40 may be added in an exemplary embodiment.

More specifically, the upper plate may include a predetermined region 11. The predetermined region 11 is a region on which the membrane 20 is seated and may be formed to have various shapes. Specifically, it may have a circular shape.

When the predetermined region 11 is formed to have a circular shape, the membrane 20 seated on the predetermined region 11 may also be formed to have a circular shape. That is to say, the membrane 20 having a shape corresponding to the shape of the predetermined region 11 may be positioned on the upper plate.

The upper plate 10 may be formed of a film or a plastic. As the upper plate 10, the lower plate 40 may also be formed of a film or a plastic. Although the upper plate 10 and the lower plate 40 may be formed of different materials, they may be formed of the same material more specifically.

More specifically, the upper plate 10 and the lower plate 40 may be formed of one or more selected from a group consisting of PVdF (polyvinylidene fluoride), nylon, nitrocellulose, PU (polyurethane), PC (polycarbonate), PS (polystyrene), PLA (polylactic acid), PAN (polyacrylonitrile), PLGA, (poly(lactic-co-glycolic acid)), PEI (polyethyleneimine), PPI (polypropyleneimine), PMMA (polymethyl methacrylate), PVC (polyvinyl chloride), PVAc (polyvinyl acetate) and a polystyrene-divinylbenzene copolymer.

The material of the upper plate 10 and the lower plate 40 is not necessarily limited to the film or the plastic and it may be replaced with various materials within the scope that can be obviously derived by those skilled in the art.

To describe the membrane 20 in more detail, the membrane 20 may be divided and defined into an upper end region and a lower end region. The upper end region is a region where the solution containing cells is contacted first and constitutes the upper end of the membrane 20. And, the lower end region is a region where the solution is contacted with the absorption means and constitutes the lower end of the membrane 20. That is to say, when the solution containing cells is discharged to one side of the upper plate 10, the solution containing cells is contacted with the upper end region. Then, the cells in the solution containing cells are left on the upper side of the membrane 20 and the remainder is contacted with the lower end region of the membrane 20 and transferred to the absorption means 30.

In an exemplary embodiment, the upper end region of the membrane 20 may have a hole with a diameter of 2 μm or smaller and the lower end region of the membrane 20 may have a hole with a diameter of 10 μm or greater. However, the diameters of the holes contained in the upper end region and the lower end region are not necessarily limited thereto and they may be changed within the ranges that can be easily derived by those skilled in the art.

In an exemplary embodiment, the membrane may be a Vivid™ plasma separation membrane.

The absorption means 30 is positioned at the lower end of the upper plate and serves to absorb the solution that has penetrated the membrane 20 from the solution containing the cells. The absorption means 30 may be seated on the lower plate 40. In an exemplary embodiment where the lower plate 40 is nonexistent, it may be coupled to the lower end of the upper plate 10.

The absorption means 30 may be formed of a filter paper or a glass fiber. However, it may also be formed of another material without being limited thereto. Accordingly, in some exemplary embodiments, the absorption means 30 may be formed of a chemical substance such as polyvinyl alcohol (PVA), polyethylene oxide (PEO) or polyacrylamide or sand.

Hereinafter, the effect of the cell separation chip according to the present disclosure or a method for separating cells using the same is described referring to FIG. 2.

FIG. 2 shows the number of surviving cells from among the cells that have been separated using the cell separation chip according to the present disclosure and then transferred to a fresh medium.

As seen from FIG. 2, when $100 \times 10^4$ cells were used for the experiment, $92.4 \times 10^4$ cells were surviving according to the prior art (control). The following results were obtained when the cell separation chip and the method for separating cells using the same according to the present disclosure were used.

Trial 1: $98 \times 10^4$ cells.
Trial 2: $97.4 \times 10^4$ cells.
Trial 3: $98.4 \times 10^4$ cells.
Trial 4: $99 \times 10^4$ cells.
Trial 5: $98.8 \times 10^4$ cells.

The prior art (control) refers to separation of cells by centrifugation. That is to say, the cell separation chip and the method for separating cells using the same according to the present disclosure showed better effect in separating cells as compared to the prior art. Also, when the cell separation chip and the method for separating cells using the same according to the present disclosure are used, mechanical loss can be minimized as compared to the prior art. Therefore, the cost of consumables can be reduced to ½ and the time required for separating the cells can be reduced.

Hereinafter, the method for separating cells according to the present disclosure is described referring to FIG. 3. In the following description, description about the same technical contents as the cell separation chip according to the present disclosure described above will be omitted to avoid redundancy.

Referring to FIG. 3, in the method for separating cells from a solution containing the cells using the cell separation chip according to the present disclosure, a step S100 wherein a solution containing cells is injected into a pipette comes first. The solution containing cells is not necessarily injected into the pipette but a small amount of the solution may also be injected into another apparatus/device. After the step S100 comes a step S110 wherein the solution containing cells injected into the pipette is discharged to the upper plate. Then comes a step S120 wherein cells from the solution containing cells are left on an upper side of the membrane. That is to say, from the solution containing cells, the cells are left on the upper side of the membrane and the remainder is passed through the membrane and absorbed by the absorption means positioned at a lower end of the membrane. In an exemplary embodiment, after the step S120, a step S130 wherein the cells left on the upper side of the membrane are transferred to a fresh cell culture medium may be further included. In addition, after the step S130, a step wherein a culture medium is sprayed from a pipette to the cells left on the upper side of the membrane so that the cells remaining on the upper side of the membrane are washed down may be further included.

According to the method for separating cells according to the present disclosure, mechanical loss can be minimized as compared to the existing centrifugation method. Therefore, the cost of consumables can be reduced to ½ and the time required for separating the cells can be reduced as described above.

The present disclosure is not limited to the exemplary embodiments described above. The above-described exemplary embodiments can be combined wholly or partly so that various modifications can be made. Accordingly, although the present disclosure has been described in detail with reference to the above-described exemplary embodiments, those skilled in the art can make modifications or changes to the exemplary embodiments without departing from the scope of the present disclosure.

It is to be noted that all the functional blocks shown in the attached drawing may not be needed to achieve the effect desired by the present disclosure and even that case may be included in the technical scope of the present disclosure defined by the appended claims.

The invention claimed is:

1. A cell separation chip for separating cells from a solution containing the cells, comprising:
   an upper plate;
   a membrane positioned on a predetermined region of the upper plate;
   an absorption device positioned at a lower end of the upper plate so as to absorb a solution which has penetrated the membrane from the solution containing the cells, and
   a lower plate positioned at the lower end of the upper plate by being connected to the absorption device,
   wherein the membrane comprises:
   an upper end region forming an upper end of the membrane as a region where the solution containing cells is contacted first, wherein the upper end region has a structure configured that cells from the solution containing cells are left on the upper end region of the membrane, the upper end region having a hole with a diameter of 2 μm or smaller; and a lower end region forming a lower end of the membrane as a region where the solution is contacted with the absorption device and the remainder of the solution are passed through the membrane and absorbed by the absorption means positioned at a lower end of the membrane, the lower end region having a hole with a diameter of 10 μm or greater.

2. The cell separation chip according to claim 1, wherein the upper plate is formed of a film or a plastic.

3. The cell separation chip according to claim 1, wherein the lower plate is formed of a film or a plastic.

4. The cell separation chip according to claim 1, wherein the absorption device is formed of a filter paper or a glass fiber.

5. The cell separation chip according to claim 1, wherein the predetermined region has a circular shape and the membrane also has a circular shape accordingly.

6. The cell separation chip according to claim 1, wherein the membrane is a plasma separation membrane.

7. A method for separating cells from a solution containing the cells, the method comprising:

injecting a solution containing cells into a pipette; and discharging the solution containing cells injected into the pipette to the upper plate of the cell separation chip of claim 1, thereby the cells from the solution containing cells are left on an upper side of the membrane, and a remainder of the solution containing cells is passed through the membrane and absorbed by the absorption device.

8. The method for separating cells according to claim 7, which further comprises, after the cells from the solution containing cells are left on the upper side of the membrane, transferring the left cells to a fresh cell culture medium.

* * * * *